(12) United States Patent
Eubisch et al.

(10) Patent No.: US 10,274,403 B2
(45) Date of Patent: Apr. 30, 2019

(54) DEVICE AND METHOD FOR DRAWING A LIQUID FROM A PROCESS TANK

(71) Applicant: Endress+Hauser Conducta GmbH+Co. KG, Gerlingen (DE)

(72) Inventors: Angela Eubisch, Chemnitz (DE); Thomas Höhne, Chemnitz (DE); Melanie Müller, Oberlungwitz (DE); Thomas Steckenreiter, Frankfurt (DE); Michael Hanko, Dresden (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 16/148,209

(22) Filed: Oct. 1, 2018

(65) Prior Publication Data

US 2019/0033176 A1 Jan. 31, 2019

Related U.S. Application Data

(63) Continuation of application No. 14/773,404, filed as application No. PCT/EP2014/053806 on Feb. 27, 2014, now abandoned.

(30) Foreign Application Priority Data

Mar. 5, 2013 (DE) .......................... 10 2013 102 127

(51) Int. Cl.
*G01N 1/14* (2006.01)
*G01N 1/28* (2006.01)
(Continued)

(52) U.S. Cl.
CPC ............... *G01N 1/14* (2013.01); *C12M 33/12* (2013.01); *C12M 37/00* (2013.01); *G01N 1/28* (2013.01);
(Continued)

(58) Field of Classification Search
CPC .. G01N 1/14; G01N 1/26; G01N 1/10; G01N 2001/002; G01N 2001/1445; C12M 33/14; C12M 33/12
See application file for complete search history.

(56) References Cited

U.S. PATENT DOCUMENTS

| 4,209,585 A | * | 6/1980 | Lloyd | .................... C12M 33/14 |
| | | | | 435/286.4 |
| 5,871,699 A | * | 2/1999 | Ruggeri | .................... G01N 1/14 |
| | | | | 422/512 |

(Continued)

*Primary Examiner* — Brian R Gordon
(74) *Attorney, Agent, or Firm* — Mark A. Logan; PatServe

(57) ABSTRACT

The application discloses a device for drawing a liquid from a process tank to be protected from contamination, including: a first receptacle for receiving the liquid withdrawn from the process tank; a first liquid line connecting the process tank with the first receptacle; and at least one first valve assembly disposed in the first liquid line and designed to block or release liquid transport through the first liquid line. The device includes at least one pressure sensor for detecting a pressure within the first receptacle. The device is designed such that a pressure difference between the first and the second ends of the first liquid line is greater than a predetermined minimum value when the first liquid line is connected with the process tank and the process tank is to be protected from contamination.

20 Claims, 7 Drawing Sheets

(51) Int. Cl.
*C12M 1/26* (2006.01)
*C12M 1/12* (2006.01)
*G01N 1/10* (2006.01)

(52) U.S. Cl.
CPC ............ *G01N 2001/1025* (2013.01); *G01N 2001/1037* (2013.01); *G01N 2001/1418* (2013.01); *G01N 2001/1445* (2013.01)

(56) References Cited

U.S. PATENT DOCUMENTS

| | | | |
|---|---|---|---|
| 2006/0027264 A1* | 2/2006 | Sann | G01N 1/14 137/212 |
| 2016/0123848 A1* | 5/2016 | Griffin | G01N 1/14 435/378 |

* cited by examiner

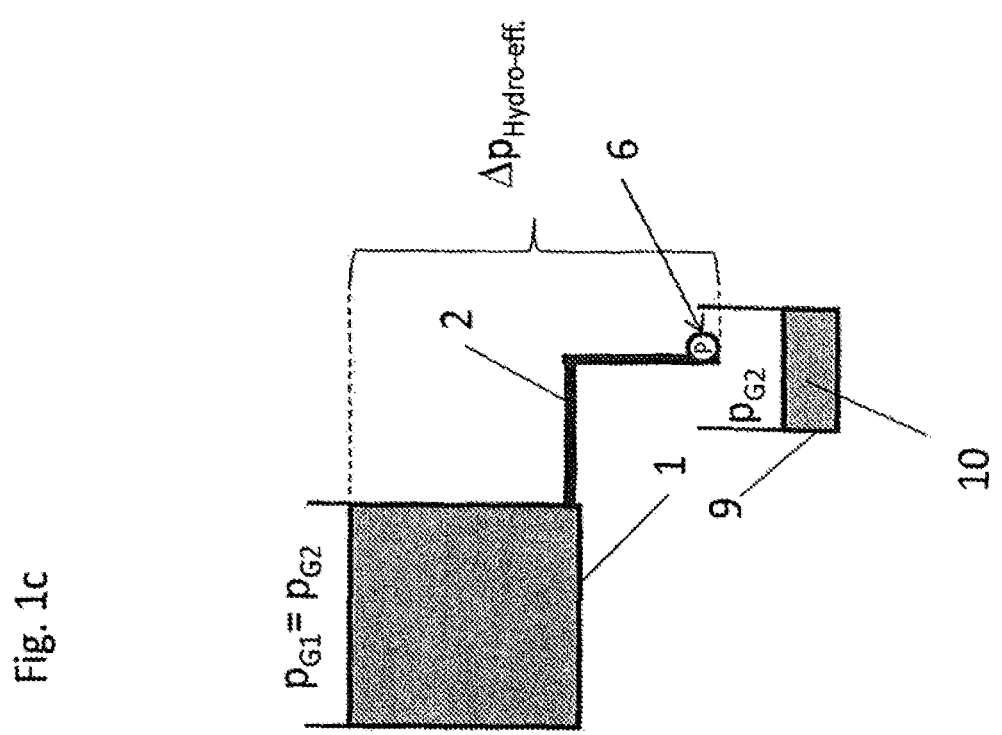

DEVICE AND METHOD FOR DRAWING A LIQUID FROM A PROCESS TANK

CROSS-REFERENCE TO RELATED APPLICATIONS

The present continuation application is related to and claims the priority benefit of U.S. patent application Ser. No. 14/773,404, filed on Sep. 8, 2015, International Patent Application No. PCT/EP2014/053806, filed Feb. 27, 2014 and German Patent Application No. 10 2013 102 127.1, filed Mar. 5, 2013, the entire contents of which are incorporated herein by reference.

TECHNICAL FIELD

The present disclosure relates to a device and method for drawing a liquid from a process tank. The present disclosure also relates to a system comprising a device for drawing a liquid from a process tank and a device for treating the drawn liquid.

BACKGROUND

Automatic or semiautomatic analytical measurement systems are used in the analytical measurement technology, for example, in industrial chemical, biotechnological, pharmaceutical and food technology processes, in the laboratory and in environmental monitoring. These are often designed to pretreat a liquid sample to be analyzed, optionally with the addition of reagents, so that in the presence of an analyte in the sample, a chemical reaction occurs which is detectable by means of physical methods, for example by optical measurements. The analyte content of the sample can be determined, for example, by irradiating the liquid sample with electromagnetic radiation, for example, visible light, from a radiation source, and the reflected radiation is received by a suitable receiver after interaction with the sample. The receiver generates a measurement signal, which depends on the intensity of the radiation received and from which the analyte content of the sample can be derived.

To use analytical method in an automated way, for example, for industrial applications or in the laboratory, it is desirable to provide a suitable automatic or semi-automatic analytical measurement system that performs the necessary analytical methods in an automated way. Such devices are known from, e.g. Published German Applications, DE 10 2009 029305 A1, DE 10 2011 11007011 A1, DE 10 2011 075 762 A1, DE 10 2011 003 615 A1 and DE 10 2011 005 957 A1.

Before the liquid sample to be analyzed is fed to the analyzer, the sample is usually pretreated, for example, by filtering. To this end, automatic or semi-automatic sample preparation devices may be used.

In many cases, the liquid samples to be analyzed are drawn from a process tank, for example, a 1media-carrying pipe or a reaction tank. The reaction tank may be, for example, a bioreactor or a fermenter. Microbial contamination of the tank and the tank contents through the environment must often be prevented for process tanks that are used in bioprocesses in the laboratory or for industrial applications. Therefore, an aseptic sampling is required in such processes. Moreover, chemical processes often need to be protected from chemical recontamination during and after sampling.

The article D. Kuystermans, Mohd A., M. Al-Rubeai, "Automated flow cytometry for monitoring CHO cell cultures", Methods 56 (3), 2012, pp 358-365, points to the importance of an automated sampling for (quasi-) real-time measurements for better monitoring and control of bioprocesses in a bioreactor, while preventing contamination of the bioreactor. This has a special significance in applications that are subject to the guidelines of the (current) Good Manufacturing Practice (cGMP) This article sets out some commercially available sampling devices for which the applicability is yet to be demonstrated in such cGMP applications.

The published international patent application WO 2010/108091 A2 describes an automated sampling device, which comprises a sampling line, which connects the process tank, from which the sample is to be taken using one or more sample tanks. The liquid sample is transported through the sampling line by a pump that is capable of bidirectional operation. In the process, the pump is meant to flush the liquid sample back into the sample tank from time to time. The sampling line and the sample tank are hermetically sealed. The ventilation ducts opening into the sampling line have a sterile filter, so that no non-sterile substances can get into the sampling line. The entire sampling device should be sterilized.

However, a disadvantage of this sampling device is the potential risk of unwanted, in particular, non-sterile substances entering the process tank due to the option of transporting the drawn liquid back into the process tank. This risk exists, for example, if the sampling device has not been successfully sterilized, or the sampling device has a leak that allows penetration of the non-sterile substances into the sampling line.

The German published patent application DE 10 2006 19 242 A1 discloses a sampling device with a sterilizable sampling valve and a transport system for feeding samples to various analyzers. The sampling valve is designed so as to be fixed on a standardized fermenter adapter of a bioreactor. It has a sample chamber of a defined volume, a front sealing element and a rear sealing element, wherein said front sealing element is opened via a connecting shaft towards the inside of the bioreactor and at the same time, the rear sealing element is sealed against the sample chamber. After closing the valve, the rear sealing element releases the path to an attached transport line.

While the device described in DE 10 2006 19 242 A1 is well suited to applications in industrial processes, its use is problematic in small fermenters in the laboratory, especially in process development, because small fermenters do not generally have suitable standardized fermenter adapters to connect the device to the fermenter. Moreover, likewise the device disclosed by Published International Application WO 2010/108091 A2, this device has no safety mechanism that prevents contamination of the bioreactor in the event that the sampling valve or associated lines are not sterile.

The German published patent application DE 102 46 262 A1 discloses a sampling device for drawing liquid samples from a tank filled with a medium, in particular, a fermenter, via a filter membrane by means of negative pressure, wherein the filter membrane arranged within a sample probe is made of a material acting as a sterile boundary, and wherein a gas feed line and a sample discharge line are arranged on the sterile boundary side of the filter membrane.

For conveying liquid in the discharge line, a negative pressure is applied to it by a pump. The liquid that is so-transferred into the discharge line is transported further by introducing an over-pressurized gas, e.g. compressed air, via the feed line, wherein the gas is passed through a sterile filter before entering the sample probe. A rinsing liquid can be passed via the feed line to the discharge line over the rear boundary of the filter membrane from time to time. The rinsing liquid is transported by the pump. Following the rinsing process, compressed air is led through the feed line to the discharge line over the rear boundary of the filter membrane to remove the rinsing liquid before a liquid sample is taken again from the tank.

During operation of the device disclosed by DE 102 46 262 A1, the rinsing liquid and compressed air reach the tank at the sterile boundary of the filter membrane. The disadvantage here is that the hydrophilic rinsing liquid may well penetrate the equally hydrophilic filter membrane in contrast to the hydrophobic compressed air. By this mass transfer it is possible that the rinsing liquid dilutes the medium, thus influencing the analyte content or the medium is discharged along with the rinsing liquid, which may also affect the bioprocess. Further, in the case of a leak in the membrane, or within the sampling probe containing the membrane, the penetration of non-sterile substances into the tank may also not be excluded here if the rinsing liquid and compressed air are contaminated due to leaks in the pipes, or a failure of the sterile filter.

SUMMARY

Therefore, the object of the present disclosure is to indicate an device that is meant to draw a liquid from a process tank and protect the content of the process tank to be protected from contamination, to an even greater extent than the generic devices known from the prior art against contamination and/or recontamination, in particular, chemical or biological contamination occurring in the device, and can continuously monitor the maintenance of this protective measure.

This object is achieved by a device for drawing a liquid from a process tank and a method for operating a device in accordance with claim 13. The present disclosure also relates to a system comprising a device for drawing a liquid from a process tank and a device for treatment of the removed liquid and a method for operating such a system.

The inventive device for drawing a liquid from a process tank, comprises:

a first receptacle for receiving the liquid drawn from the process tank;

a first liquid line that connects the process tank with the first receptacle and has a first end that can be connected to the process tank and a second end that opens into the first receptacle; and at least one first valve assembly, which is arranged between the first and second ends of the first liquid line and is adapted to selectively block or allow liquid transport through the first liquid line, wherein the device comprises at least one pressure sensor, which is connected with the first receptacle, in particular, for detecting a pressure within the first receptacle, and/or is arranged at the second end of the first liquid line, wherein the device is designed to transport liquid in a first operating mode from the process tank to the first receptacle, and wherein the device is designed to block transport of a liquid in a second operating mode from the process tank to the first receptacle, wherein the device is designed such that both in the first operating mode and the second operating mode and as long as the first end of the first liquid line is connected with the process tank and as long as the process tank must be protected from contamination, there is a pressure difference $p_1-p_2$ between the pressure $p_1$ at the first end of the first liquid line and the pressure $p_2$ at the second end of the first liquid line that is greater than or equal to zero, in particular, greater than a predetermined allowable minimum value.

A process tank refers here and hereinafter to a tank containing a medium to be monitored that can be, in particular, a medium used or produced in, for example, a biological or biochemical process. A process tank can be, for example, a large-scale bioreactor or fermenter made of steel, a bioreactor or fermenter made of a disposable film or a glass body, in particular, a fermenter for laboratory applications or process development, or a medium-carrying pipe or hose line. Preferably, the medium contained in the process tank is a process medium of a chemical, biological or biochemical process to be protected from contamination, in particular, chemical or biological contamination.

The process tank and the receptacle can be designed as a closed tank, which are optionally connected via sterile filter with pressure equalization openings or with pressure transducers, for example, gas pressure regulators, which are designed to control and/or regulate the pressure in each of the tanks to a predeterminable value.

The liquid to be drawn may be an essentially particle-free liquid or also particle-containing liquid. The particles can be, for example, cells, cell components or cell aggregates.

The first valve assembly, which is arranged between the first and second ends of the first liquid line and is designed to selectively block or allow liquid transport through the first liquid line, divides the liquid line into a first part, starting from the process tank up to the valve assembly, and a second part from the first valve assembly up to the first receptacle. A valve assembly refers here and hereinafter to an assembly which provides a valve function, i.e. enabling or disabling a liquid or gas line. It may comprise at least one valve, i.e. it may be formed of a single valve or comprise one or more valve(s). In addition to a valve, a valve assembly may also comprise additional components with other functions. This allows interruption of the removal of the liquid from the process tank, wherein the pressure difference existing between the first and the second ends of the first liquid line, i.e. the pressure difference $p_1-p_2$, formed between the pressure $p_1$ and at the first end of the first liquid line and the pressure $p_2$ at the second end of the first liquid line, is greater than zero or the allowed minimum value, even with interruption of the removal of the liquid, i.e. with the first liquid line blocked by the valve assembly, as long as the first end of the liquid line is connected to the process tank and as long as the process tank must be protected from contamination.

At least the drawn liquid medium that is inside the second section of the first liquid line is transported from the process tank through the second part of the first liquid line to the first receptacle by the fact that the pressure difference $p_1-p_2$ between the first and the second ends of the first liquid line, comprising at least one first valve assembly arranged between the first and the second ends of the first liquid line, is greater than zero or greater than or equal to, in particular, a positive, allowed minimum value in the first operating mode and in the second operating mode of the device, i.e. the pressure $p_1$ at the first end of the first liquid line is greater than the pressure $p_2$ at the second end of the first liquid line, in both operating modes. This ensures that the medium, in particular, the drawn liquid within the second part of the first liquid line, i.e. in the part of the liquid line extending between the first valve assembly and the first receptacle, is transported away from the process tank and not back into the process tank. Thus, chemical or biological contamination of the process tank is effectively prevented even if it occurs in the second part of the first liquid line, which is in constant contact with the first receptacle, and thus, more prone to contamination due to leaks or lack of sterilization of the first receptacle or second portion of the first liquid line or associated components.

The allowed minimum value may be, in particular, other than zero. To set the allowed minimum value of the pressure difference, the hydrostatic pressures which prevail at the first and second ends of the first liquid line, and the respective gas pressures in the first receptacle and process tanks are crucial. Without initial consideration of the gas pressure prevailing in the tank i, a general analysis results in a pressure difference $\Delta p_{Hydro,i}$ which acts due to the prevailing hydrostatic pressures, as illustrated in FIG. 1a, at the end of a liquid line that leads to a tank i with liquid, and arises from the difference between the hydrostatic pressure $p_{Hydro,Leitung,i}$ through the liquid column present in the liquid line and the hydrostatic pressure $p_{Hydro,Behälter,i}$ through the liquid column outside the line in the tank i between the end of the line and the liquid surface in the tank:

$$\Delta p_{Hydro,i} = p_{Hydro,Leitung,i} - p_{Hydro,Behälter,i} \quad (1)$$

An effective hydrostatic differential pressure $\Delta p_{Hydro\text{-}eff}$, arises from the difference between $\Delta p_{Hydro,1}$ and $\Delta p_{Hydro,2}$ if a first tank, for example, the mentioned process tank 1, and a second tank, for example, the first receptacle 9, are connected by a liquid line 2, as illustrated in FIG. 1b:

$$\Delta p_{Hydro\text{-}eff} = \Delta p_{Hydro,1} - \Delta p_{Hydro,2} \quad (2)$$

A gas pressure $p_{G1}$ also prevails in the first tank and a gas pressure $p_{G2}$ in the second tank. The pressure $p_1$ that prevails at the first end of the liquid line connected to the said process tank 1 (the first tank) is given by the difference between $p_{G1}$ and $\Delta p_{Hydro,1}$, while the pressure $p_2$ that prevails at the second end of the liquid line connected to the said first receptacle 9 (the second tank) is correspondingly given by the difference between $p_{G2}$ and $\Delta p_{Hydro,2}$. The pressure difference between the first and the second end of the first liquid line, namely $p_1-p_2$, is greater than zero or greater than or equal to, in particular, a positive, allowed minimum value, during operation of the device in its first and in its second operating modes, if it is ensured that the difference between the gas pressure in the first tank $p_{G1}$ and the effective hydrostatic differential pressure $\Delta p_{Hydro\text{-}eff}$ is greater than the gas pressure in the second tank $p_{G2}$:

$$p_{G1} - \Delta p_{Hydro\text{-}eff} > p_{G2} \quad (3)$$

An allowed minimum value of the pressure difference can be specified as a set point for regulation of the pressure difference. The allowed minimum value is preferably identical for the first and second operating modes. However, different allowed minimum values can be specified for the first and the second operating modes.

Additional safety is provided by the pressure sensor that is connected with the first receptacle and/or arranged at the second end of the liquid line. Based on the measurement signal produced by this sensor, the pressure difference between the first and the second ends of the liquid line can be monitored. Thus, the measurement signal of the pressure sensor can be used, in particular, to detect leaks, for example, leakage of the first receptacle, the liquid line or the valve assemblies arranged in the liquid line. This can be done by an operator or an automatic control unit.

The device can be also be designed, in particular, to control and/or regulate the pressure difference $p_1-p_2$ between the first and second ends of the first liquid line, on the basis of the measurement signal output from the pressure sensor. Using the pressure sensor signal, monitoring and/or control of a liquid transport in said first liquid line to the receptacle can also take place.

In an advantageous embodiment, the device may comprise a control unit that is designed, in particular, to monitor the pressure difference $p_1-p_2$ between the first and the second ends of the first liquid line and/or to control and/or to regulate this pressure difference, on the basis of the measurement signal from the pressure sensor. In order to control and/or regulate the pressure difference between the first and the second ends of the liquid line, the control unit can directly regulate the pressure difference, based on measurements of the pressures prevailing at the first and/or second ends of the liquid line, or measured variables representing them. The control unit can be used to regulate said pressure difference, as well as one or more variables influencing the pressure difference, for example, to control and/or regulate a gas pressure prevailing in the first receptacle and/or the gas pressure prevailing in the process tank, or a fill level in the process tank, in the liquid line or in the first receptacle. In the case of such a control and/or regulation of the pressure difference by control and/or regulation of the variable influencing the pressure difference, the control variable (the set point) can be specified such that the pressure difference between the first and second ends of the liquid line is greater than zero, in particular, greater than a predetermined minimum value.

The control unit may comprise one or more gas pressure regulator(s) or be connected with one or more gas pressure regulator(s) that is/are connected with the first (closed) receptacle in such a way that the one or more gas pressure regulator(s) can influence at least the gas pressure within the first receptacle $p_{G2}$, and thus, the pressure $p_2$ at the second end of the first liquid line. The control unit may be also designed such that it detects leakage in the device, based on the measurement signal from the pressure sensor.

The control unit may comprise an electronic data processing device, such as a transmitter, a programmable logic controller (PLC), a process control computer, a PC, a laptop, a tablet PC or a smartphone. It may also comprise, in particular, a plurality of separate units that are interconnected for communication, such as a central transmitter or control computer, which is connected to one or several controllers. It may comprise a computer program, which is used for processing the measurement signals from the pressure sensor, for monitoring the pressure difference between the first and the second ends of the first liquid line and/or for detecting any leaks and may be stored, for example, in one or more interconnected or spatially separated memories of the control unit, and it can be configured to execute this computer program. The control unit, in particular, the computer program, can be configured to output an alarm signal upon detection of a leak, for example, a detected pressure drop or exceeding specified tolerance ranges.

The device is designed to ensure that the pressure difference between the first and the second ends of the first liquid line is at any time greater than or equal to zero, in particular, greater than or equal to the allowed minimum value in the first and in the second operating mode of the device, as long as the process tank must be protected against contamination and the first end of the transport line is connected to the process tank, posing the risk that potentially contaminating substances can pass from the first liquid line into the process tank. To this end, the first liquid line can open into the process tank and the first receptacle can be arranged in relation to the process tank in such a way that the allowed pressure difference is ensured from the onset due to the hydrostatic pressure in the process tank and in the first liquid line. Such an arrangement is schematically shown, for example, in FIG. 1c.

If the device, as already mentioned, comprises a control unit, it may also be possible that the control unit is designed to control and/or regulate the pressure difference between the first and the second ends of the first liquid line so that it is always greater than zero, especially greater than an allowed minimum value as long as the first end of the first liquid line is connected to the process tank and the process tank must be protected from contamination. To this end, the control unit may comprise a gas pressure regulator which is designed to regulate the gas pressure in the first receptacle to a predetermined value on the basis of the measurement signal from the pressure sensor. The set point can be determined and specified on the basis of a known pressure or that measured in the process tank and on the basis of known data on the fill level in the process tank and geometric conditions of the process tank and the first receptacle.

Contamination of the process tank must particularly be avoided if and insofar as the liquid to be drawn from the device is present in the process tank. Contamination of the process tank can also be avoided when sterilization of the process tank and the connected first liquid line, and of the first receptacle connected to the liquid line (a so-called SIP (sterilization in place)) is completed before the actual process is started in the process tank.

The device can be designed to determine on the basis of a control signal whether the process tank must be protected against contamination at a given time, so as to ensure that there is a pressure difference between the first and the second ends of the first liquid line, both in the first and in the second operating modes of the device, and as long as the first process tank must be protected from contamination. This control signal can be generated, for example, by manual input of an operator. Alternatively, the control signal can be provided by a process control system of the device, for example, a process control of the process performed in the process tank.

The control signal can represent, for example, the beginning of a time interval during which the process tank must be protected from contamination. The control unit may be designed to maintain the pressure difference between the first and the second ends of the liquid line greater than zero at all times, upon receipt of the control signal. The control unit may also be adapted not to actively control or regulate the pressure difference any longer, upon receipt of a second control signal that represents the end of the time interval during which the process tank must be protected from contamination.

Alternatively, the control signal may represent the beginning and end of a predetermined time interval during which process the tank must be protected from contamination. The control unit may be designed in this case to control and/or regulate the pressure difference between the first and second ends of the first liquid line to a value greater than zero at any given time during the predetermined time interval.

If the device includes a control unit, as already mentioned above, this may be designed to receive and evaluate the control signal, and on the basis of the control signal, to perform the monitoring, control and/or regulation of the pressure difference between the first and the second ends of the first liquid line, or of at least one variable having an effect on the pressure difference, so as to ensure a pressure difference between the first and second ends of the first liquid line that is greater than or equal to zero, in particular, greater than the predetermined allowed minimum value, both in the first operating mode and the second operating mode and as long as the first process tank must be protected from contamination. For this purpose, the control unit, as already mentioned, can regulate, in particular, a gas pressure in the first receptacle and/or in the process tank, as the gas pressures, prevailing in the first receptacle and in the process tank, act on the pressure difference between the first and second ends in the first liquid line as described above.

If there is a need to protect the process tank from contamination because the cleaning and sterilizing medium is fed into the process tank, and not because, e.g. the process tank is cleaned and/or sterilized before being used for carrying out a process, it is also not necessary to maintain a pressure difference of greater than zero between the first and the second ends of the first liquid line. Before and during sterilization, which is carried out usually under pressure, the process tank need not be protected against contamination by media flowing back from the first liquid line.

In one embodiment of the device, the first end of the first liquid line opens into the process tank. In this embodiment, the first end of the liquid line is always connected to the process tank.

In an alternative embodiment, the first liquid line can have a sluice valve, which is designed either to connect the first end of the first liquid line with the process tank or to shut off the first end of the first liquid line from the process tank. To this end, the sluice valve can be designed, so as to traverse the first end of the first liquid line between a first position, which is retracted into the process tank and in which the first end is connected to the process tank, and a second position, which is extended from the process tank and in which the first end is not connected to the process tank. If the first end of the first liquid line is separated from the process tank by the sluice value, no liquid can be removed and return flow of contaminated liquid into the process tank is prevented. Therefore, in this state, the pressure difference between the first and the second ends of the device need not necessarily be maintained.

If the device has the above-mentioned control unit, it is possible that it controls the sluice valve on its own or is connected to a control system of the sluice valve for communication. In both cases, the control unit may be designed to determine whether the first end of the first liquid line is connected to the process tank, based on the current position of the sluice valve, and as long as this is the case, to monitor or control and/or regulate the pressure difference between the first and the second ends of the liquid line.

In one possible embodiment, the pressure difference between the first and the second ends of the first liquid line is achieved by the fact that the first liquid line opens out into a portion of the process tank that is filled with liquid during operation of the device and is designed such that a negative effective hydrostatic differential pressure $\Delta p_{Hydro-eff}$ is obtained, based on the above equations (1) and (2). If the gas pressure $p_{G1}$ in the process tank and the gas pressure $p_{G2}$ in the first receptacle are identical, liquid is transported in this way from the process tank towards the first receptacle, which is preferably connected with the ambient environment via a sterile filter for pressure equalization. The gas pressure $p_{G1}$ in the process tank could be regulated to a predetermined value using a process control system. In this embodiment, the pressure sensor can be arranged at the second end of the first liquid line to monitor the pressure therein, and to detect any leakage.

In another possible embodiment, the pressure difference between the first and the second ends of the first liquid line can be achieved, in particular, by means of the mentioned control unit by the fact that a gas pressure prevailing in the first receptacle is adjusted such that the pressure prevailing at the second end of the first liquid line is lower than the pressure at a first end of the first liquid line by at least the allowable minimum value, during both the first as well as the second operating modes of the device. For this purpose, a gas pressure can be generated in the first receptacle, which is below the difference between the gas pressure $p_{G1}$ prevailing in the process tank and the effective hydrostatic differential pressure $\Delta p_{Hydro\text{-}eff.}$ defined in equation (2). by at least a predetermined minimum value M (see equation (3)):

$$p_{G2}=p_{G1}-\Delta p_{Hydro\text{-}eff.}-M \quad (4)$$

To this end, the gas pressure prevailing in the process tank $p_{G1}$ can be measured and the effective hydrostatic differential pressure $\Delta p_{Hydro\text{-}eff.}$ can be determined. A measurement of the gas pressure prevailing in the first process tank can be omitted if the pressure prevailing in the process tank is known. For example, in biological processes with cell cultures, the internal pressure prevailing in the process tank is often regulated to a slight positive pressure between 20 mbar and 100 mbar. The control variable (set point) of the regulation can then enter the control and/or regulation of the gas pressure in the first receptacle as a known value. The effective hydrostatic differential pressure $\Delta p_{Hydro\text{-}eff.}$ can be determined from the geometrical arrangement between the process tank, the first receptacle and the first liquid line with sufficient approximation. A measurement of the pressures prevailing at the ends of the liquid lines is, of course, possible. If necessary, the fill levels of liquid in the process tank and the first receptacle can also be measured. The predetermined minimum value M corresponds to the allowable minimum value of the pressure difference between the first and the second ends of the first liquid line in the first approximation. In this embodiment, the pressure sensor correlates with a gas volume contained in the first receptacle for detecting the gas pressure prevailing inside the first receptacle. The control unit may be equipped with, in particular, a gas pressure regulator to control and/or regulate the gas pressure $p_{G2}$ prevailing in the first receptacle—in the first and in the second operating modes of the device as long as the process tank is to be protected from contamination and as long as the first end of the liquid line is connected to the process tank—such that this gas pressure $p_{G2}$ falls below the difference between the gas pressure $p_{G1}$ prevailing in the pressure tank and the effective hydrostatic differential pressure $\Delta p_{Hydro\text{-}eff}$ in equation (2) by at least a predetermined minimum value M, see equation (4).

The device may comprise a gas line, which opens into the first receptacle and can be used to adjust, in particular, to control or regulate the gas pressure prevailing in the first receptacle. The pressure sensor may be connected to the first receptacle via this gas line to monitor the gas pressure prevailing in the first receptacle.

The gas line can connect the first receptacle with a gas pressure regulator, which is used for controlling and/or regulating a gas pressure prevailing in the first receptacle, based on, in particular, a measurement signal that is output by the pressure sensor. The gas pressure regulator can be a component of the aforementioned control unit.

The gas pressure regulator can be designed to control or regulate the gas pressure prevailing in the first receptacle such that the gas pressure prevailing in the first receptacle leads to the fact that the pressure prevailing at the second end of the first liquid line is lower than the pressure prevailing at the first end of the first liquid line by at least the minimum allowed value. To this end, the gas pressure regulator may be designed to set a gas pressure in the first receptacle in accordance with equation (4). The gas pressure regulator may comprise, for example, a pump device, in particular, a vacuum pump, diaphragm pump or a peristaltic pump, which is connected to a control unit. The control unit can be a component of the pump device or part of the aforementioned control unit that is spatially separated from the pump device, but connected for data communication.

A sterile filter may be arranged in the gas line, in particular, between the gas pressure regulator and the first receptacle. Preferably, the pressure sensor is also separated from the first receptacle by the sterile filter, as far as it is connected to the first receptacle via the gas line.

In an advantageous embodiment, the first liquid line may have a constant and/or adjustable and/or controllable flow resistance, in particular, an adjustable hose pinch valve. This may be used to adjust a desired flow resistance in the first liquid line during the removal of the liquid with the valve assembly open to allow more precise metering.

The second end of the first liquid line can lead to the first receptacle in such a way that the liquid escaping there passes through a gravity section. In this way, any chemical or biological contamination contained in the first receptacle is prevented from reaching the first liquid line, as the fill level of the first receptacle does not come in contact with the second end of the first liquid line.

In one embodiment, the device may include a fill level detector for detecting the fill level of the liquid contained in the first receptacle. In particular, the device can be designed to issue an alarm when the level exceeds a predetermined threshold. Based on the alarm, an operator or a control unit of the device can prevent the second end of the first liquid line from coming in contact with the liquid contained in the first receptacle by performing an operation in the device.

The device may comprise a second liquid line, which is different from the first liquid line, flows into the first receptacle, and is used to drain the liquid from the first receptacle. This second liquid line can be closed by a valve assembly. In an advantageous embodiment, the second liquid line, whose end that does not lead into the first receptacle, has a coupling device for connecting the first receptacle with an analyzer or a device for treatment of the liquid contained in the first receptacle. Furthermore, the device may have an additional liquid line, which is different from the first and second liquid lines, opens into the first receptacle, can be closed by a valve assembly and whose second end is connected to a tank containing a rinsing and or cleaning solution. This embodiment allows rinsing and/or cleaning of the first receptacle between two sampling operations, while the pressure difference between the first and the second ends of the first liquid line is maintained greater than zero.

In an advantageous embodiment of the device, the first receptacle and the first liquid line may be connected with the gas line and optionally, with the sterile filter, so as to allow replacement and sterilization. Advantageously, the first receptacle, the first liquid line, the gas line, the sterile filter and the second liquid line are designed as a modular unit that can be sterilized by itself or in conjunction with the process tank.

In a method for operating a device for drawing a liquid from a process tank, in particular, a device according to one of the embodiments described above, the process tank to be protected from contamination and a first receptacle for receiving the liquid extracted from the process tank are connected by a first liquid line, which has a first end that can be connected to the process tank and a second end opening into the first receptacle, liquid is transported from the process tank to the first receptacle in a first operating mode, and wherein a liquid transport from the process tank to the first receptacle is blocked in a second operating mode, wherein a pressure difference that is greater than zero, especially greater than or equal to a predetermined allowed minimum value is applied between the first and the second ends of the first liquid line, in both the first and the second operating modes and as long as the first and second end of the first liquid line is connected to the process tank and as long as the process tank is to be protected from contamination, wherein blocking of liquid transport from the process tank into the first receptacle is by means of a valve assembly, which is arranged between the first and second ends of the liquid line and is adapted to block or release liquid transport through the first liquid line.

The pressure difference may be monitored by means of a pressure sensor that is connected with the first receptacle, in particular for detecting a pressure prevailing in the first receptacle.

The allowed minimum value is preferably identical for the first and second operating modes according to the above equation (3). However, the allowed minimum value may be set differently for the first and second operating modes.

In this embodiment of the method, the pressure difference between the first and the second ends of the first liquid line is at all times greater than or equal to the permissible minimum value during operation of the device in the first and in the second operating modes of the device, wherein this pressure difference can be monitored by means of the measurement signal of the pressure sensor.

In one embodiment, the pressure difference or a variable influencing the pressure difference can be controlled and/or regulated such that it is greater than zero, especially greater than or equal to a predetermined allowed minimum value, in particular, on the basis of the measurement signal of the pressure sensor.

As previously described, the pressure difference between the first and the second ends of the first liquid line can be less than zero or below the minimum allowed value during performance of process steps, in which protection of the process tank from contamination is not required, for example, before or during sterilization of the process tank, so that liquid from the first receptacle or from the first liquid line can pass into the process tank. Therefore, monitoring of the pressure difference, or its control and/or regulation or the control and/or regulation of the variable influencing the pressure difference may be omitted as long as the process tank is not to be protected from contamination, for example, during cleaning and sterilization measures, or as long as the first end of the first liquid line is separated from the process tank by, for example, the previously mentioned sluice valve.

The pressure sensor can be connected with the first receptacle, in particular, for detecting a pressure within the receptacle, and/or be arranged at the second end of the first liquid line.

In an advantageous embodiment of the method, the pressure difference is controlled and/or regulated by generating a gas pressure in the first receptacle that is lower than the difference between the gas pressure $p_{G1}$ prevailing in the process tank and the effective hydrostatic differential pressure $\Delta p_{Hydro\text{-}eff.}$ by at least a predetermined minimum value M (cf. equation (4)). The predetermined minimum value corresponds to the allowed minimum value of the pressure difference between the first and the second ends of the first liquid line in the first approximation.

In this method, specified liquid volumes, which may always be similarly or differently dimensioned, as needed, can repeatedly be transferred from the process tank to the first receptacle.

Here, the transport of the liquid can be carried out from the process tank to the first receptacle by controlled increase in the pressure difference.

To draw a defined volume of liquid from the process tank and to transfer it into the first receptacle, the pressure difference between the first and second ends of the first liquid line can be increased in a first step, with the first liquid line blocked. In a second step, the first liquid line can be released, whereby liquid is transported from the process tank towards the first receptacle. In a third step, the first liquid line can be blocked again. This ensures that the pressure difference is less than the allowed minimum value at any time.

In an advantageous embodiment of this method, the liquid volume drawn from the process tank is determined, based on the increase in gas pressure in the first receptacle, detected by the pressure sensor during the liquid transport.

The present disclosure also relates to a system, comprising a device for drawing a liquid from a process tank according to one of the preceding embodiments, and a device for treatment of the drawn liquid.

In one embodiment of the system, the device for treatment of the liquid comprises at least a second receptacle, which is different from the first receptacle and is connected, in particular, in a detachable manner to the first receptacle via a third liquid line that opens into the second receptacle, so as to transport liquid from the first receptacle to the second receptacle. By means of a coupling device, the third liquid line may be connected in a detachable manner to the second liquid line that opens into the first receptacle. Alternatively, the second and third liquid lines may also be formed as sections of a single liquid line.

The device for treatment of the liquid can be designed to separate particles, in particular cells, cell components and/or cell aggregates, from the liquid, in particular, at least 25% of the particulate matter contained in a given unit volume of the liquid. Preferably, the device is designed to separate particles by at least 50%, preferably at least 75%, of the particulate matter contained in a given unit volume of the liquid.

The device for the treatment of the liquid may comprise a gas pressure control unit that is connected to the second receptacle for setting a gas pressure in the second receptacle. Likewise the gas pressure regulator connected to the first receptacle, the gas pressure control unit may comprise a gas pressure regulator that may have, for example, a pumping device, in particular, a vacuum pump, diaphragm pump or a peristaltic pump, which is connected to a control unit. The control unit can be a component of the pump device or part of a control unit that is spatially separated from the pump device, but connected for data communication. In particular, this control unit may be identical to the control unit of the previously described device for drawing a liquid from the process tank, or be connected to it for communication. Monitoring, control and regulation of the liquid transport between the first and the second receptacles can be performed on the basis of the measurement signal of the pressure sensor that is in communication with the first receptacle, and a measurement signal of a pressure sensor that is in communication with the second receptacle.

The device for the treatment of the liquid can have at least one particle separation module comprising, in particular, a sterile filter for separating the particles. The particle separation module can comprise, in particular, one or more filter membranes. Furthermore, the particle separation module may comprise a device for separating particles due to their inertia, by using, for example, sedimentation or centrifugation method.

The device for treatment of the liquid may comprise a fourth liquid line, which is different from the third liquid line, opens into the second receptacle and is connected in a detachable manner with a fifth liquid line over the particle separation module, in particular, via a coupling device. A pressure sensor that detects the gas pressure in the second receptacle can allow monitoring, control and regulation of liquid transport within the fifth liquid line.

The fifth liquid line may include a first branching point, such as a T-piece, over which liquid can be drawn from the fifth liquid line. The branching point can be connected, for example, with an analyzer, in particular an automated analyzer, comprising a biosensor. The liquid can be supplied to the analyzer in this way as a liquid sample to be analyzed.

The fifth liquid line may comprise a second branching point, over which the fifth liquid line can be connected with at least one reservoir, containing a cleaning and/or disinfecting liquid.

At least one of the liquid lines of the device for drawing a liquid from the process tank and/or at least one of the liquid lines of the device for treatment of the liquid may comprise at least one sensor, in particular, a conductivity sensor, which is designed to detect a fill level of the liquid line. The measurement signal of a conductivity sensor arranged in a liquid line shows a clearly noticeable change if gas is present at the installation location of the conductivity sensor instead of the liquid to be transported in the liquid line or if the liquid present at the installation location of the conductivity sensor has gas bubbles. Therefore, the signal of the at least one conductivity sensor can be used to control the liquid transport, especially with the aim of avoiding the pumping of gas or gas bubbles into the particle separation module. The measurement signal of the conductivity sensor can be used alternatively or additionally for monitoring and/or controlling the transport of predetermined volumes of liquid, wherein it can be determined on the basis of the measurement signal when a transportable liquid volume has reached the installation location of the conductivity sensor or when the liquid volume has crossed the installation location of the conductivity sensor.

The device for drawing the liquid from the process tank and/or the device for treating the liquid may be designed as a module separable from the rest of the system in each case. Depending on the requirements of the specific analytical application, the device for drawing the liquid from the process tank and the device for treatment of the liquid may be connected to one another via at least one liquid line, and be arranged spatially separated from each other.

A method for operating the system, in particular, according to one of the embodiments described above, comprising a device for drawing a liquid from a process tank, in particular, according to one of the embodiments described above, and a device for treatment of the withdrawn liquid comprises a first operating mode, in which liquid is transported from a first receptacle of the device, which is used for drawing a liquid from a process tank through a liquid line which connects the first receptacle to a second receptacle of the device for treatment of the withdrawn liquid, into the second receptacle, wherein the gas pressure prevailing in the second receptacle for conveying the liquid is adjusted such that it is lower than the gas pressure prevailing in the first receptacle.

The first operating mode of the method for operating the system may comprise another step of feeding liquid from the second receptacle into a liquid line that is connected to the second receptacle via a particle separation module. Liquid can be removed via a branch of the liquid line and fed, in particular, to an analyzer connected to the system.

The method for operating the system may comprise a second operating mode, in which the particle separation module is backwashed for cleaning and/or disinfection. Backflushing refers to the transport of liquid through the particle separation module, in particular, the filter membrane or filter membranes, in the direction of the second receptacle.

The second operating mode of the method for operating the system may further include treating at least a portion of the surfaces of the system, in contact with a liquid, using a cleaning and/or disinfecting liquid. In particular, the cleaning and/or disinfecting liquid can be conveyed from at least one reservoir, which is connected with the second receptacle over a branching point of a liquid line that opens into the second receptacle via the particle separation module.

In another embodiment, backflushing can also include the transport of liquid through the third liquid line towards said second receptacle. To this end, the third liquid line may comprise an additional branching point, over which the third liquid line can be connected with at least one reservoir, containing a cleaning and/or disinfecting liquid.

The unwanted closure of the liquid lines and/or the clogging of the filter membranes is prevented by cleaning. Disinfection represents an additional protection of the system against contamination and also prevents contaminations of the liquid sample to be analyzed by any microbial activity between two sampling and treatment processes. For example, 70 vol.-% ethanol or isopropanol can be used as a disinfectant liquid.

As a cleaning liquid, pure water, preferably with a conductivity of 500 µs/cm to 700 µs/cm corresponding to that of tap water and/or phosphate buffered saline, and/or 10 mM tris-buffer and/or 0.5 mM sodium pyrophosphate with 0.7 mM tri-Na-EDTA can optionally be used in each case with at least one surfactant such as Tween 20 or Tween 80. Additionally, or alternatively, it may be advantageous to use a highly concentrated, buffered saline as the cleaning liquid. During backflushing with such liquids, a high osmotic pressure gradient develops in the cell-containing particles left in the particle separation module, thus forcing water out of the interior of the cell-containing particles. This leads to a volume reduction, which allows removal of the particles by backflushing.

In another embodiment, the backflush process may be associated with the use of an additional temperature control for the cleaning liquid, wherein the cleaning liquid is gradually heated during the cleaning process, starting from a low temperature within or below the room temperature range to at least 50° C. to 80° C.

BRIEF DESCRIPTION OF THE DRAWINGS

The present disclosure is explained in more detail below with reference to the exemplary embodiments illustrated in the drawings:

FIG. 1c is a schematic diagram of a second device for drawing a liquid from a process tank;

DETAILED DESCRIPTION

Figure 1B:
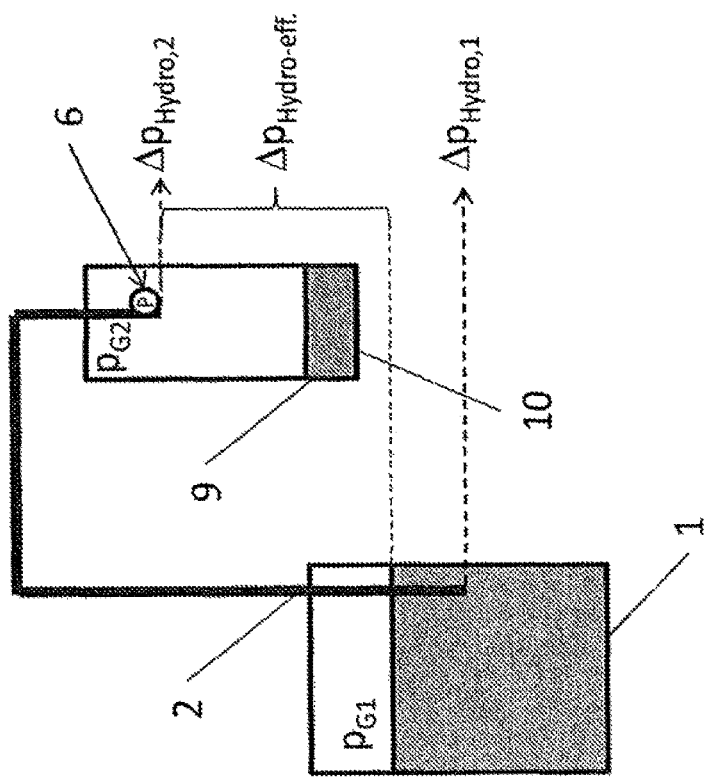
FIG. 1b is a schematic diagram of a first device for drawing liquids from a process tank.
Figure 1A:
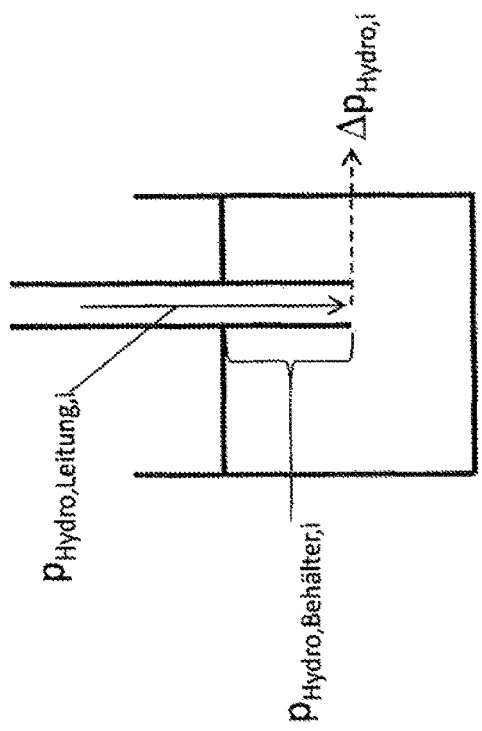
FIG. 1a is a schematic diagram for explaining the interaction of the hydrostatic pressure at the end of liquid line that flows into a tank.

FIG. 1a shows schematically the correlation of the pressure difference $\Delta p_{Hydro,i}$ due to the prevailing hydrostatic pressures at the end of a liquid line that generally opens into a tank i, without consideration of the gas pressure. This is calculated from the difference between the hydrostatic pressure $p_{Hydro,Leitung,i}$ through the liquid column present in the liquid line and the hydrostatic pressure $p_{Hydro,Behälter,i}$ through the liquid column outside the line in the tank i, between the end of the line and the liquid surface in the tank.

FIG. 1b shows schematically a device for drawing a liquid from a process tank 1 and transferring it to a receptacle 9, which receives the drawn liquid 10. The process tank 1 is connected with the receptacle 9 via a liquid line 2, which has a first end connected to the process tank 1 and a second end which opens into the receptacle 9. In this example, the first end of the liquid line 2 is designed as a riser that dips into the liquid contained in the process tank. The effective hydrostatic differential pressure ΔpHydro-eff. Results from the difference between $\Delta p_{Hydro,1}$ and $p_{Hydro,2}$, also $p_{Hydro,1} - \Delta p_{Hydro,2}$ and is positive in this embodiment (according to equations (1) and (2)). A gas pressure $p_{G1}$ prevails in the process tank 1 and a gas pressure $p_{G2}$ in the receptacle 9. During operation of the device shown in FIG. 1b, it is ensured at all times that the pressure difference $p_1-p_2$ between the first and the second ends of the liquid line 2 is greater than zero, in particular, greater than or equal to an allowed minimum value (in accordance with equations (3) or (4)). A pressure sensor 6, which is arranged within the receptacle 9 at the second end of the liquid line 2, is used to monitor compliance with this condition. The pressure at the second end of the liquid line 2 must be lower than that at the first end of the liquid line 2 for liquid transport from the process tank 1 into the receptacle 9. For this purpose, the pressure $p_2$ at the second end of the liquid line 2 or the gas pressure $p_{G2}$ in the receptacle 9 is set accordingly in the embodiment shown here. If this is automated by means of a control unit, a pressure value that represents the pressure $p_1$, prevailing in the first tank 1, in particular, at the first end of the liquid line 2, can be provided to the control unit for this purpose.

FIG. 1c shows an example of a device for drawing and transferring a liquid from a process tank 1 to a receptacle 9, which is connected to the process tank 1 via a liquid line 2 and is designed such that a pressure difference $p_1-p_2$ occurs between a first end of the liquid line 2, which is connected to the process tank 1, and a second end of the liquid line 2, which opens into the receptacle 9, wherein said pressure difference causes liquid transfer from the process tank 1 to the receptacle 9, without the need for any additional mechanism for adjusting the pressure difference, in particular, without a control or regulation of the pressure prevailing at the second end or the pressure prevailing in the receptacle 9. The liquid line 2 opens at its first end into a lower region of the process tank 1, which is normally below the level of the liquid contained in the process tank 1 during operation of the device. The liquid line 2 also extends such that the pressure difference $\Delta p_{Hydro,2}$ prevailing at the second end of the liquid line 2 is higher than the corresponding pressure difference $p_{Hydro,1}$ at the first end of the liquid line, so that (according to equation (2)), the effective hydrostatic differential pressure ΔpHydro-eff is negative. In this example, atmospheric pressure prevails in the process tank 1 and the receptacle 9, and thus, the same gas pressure. Therefore, the difference between the gas pressure $p_{G1}$, prevailing in the process tank 1, which is equal to atmospheric pressure in this case, and the effective hydrostatic differential pressure ΔpHydro-eff. is always greater than the atmospheric pressure, and thus, always greater than $p_{G2}$, because the receptacle is in contact with the surroundings at atmospheric pressure (see equation (3)).

This always ensures that the pressure difference $p_1-p_2$ between the pressure $p_1$ prevailing at the first end of the liquid line 2 and the pressure $p_2$ prevailing at the second end of the liquid line is greater than zero or greater than or equal to a predetermined minimum value allowed. A pressure sensor 6 that is arranged at the second end of the liquid line 2 is used to monitor compliance with the pressure difference.

Figure 2:
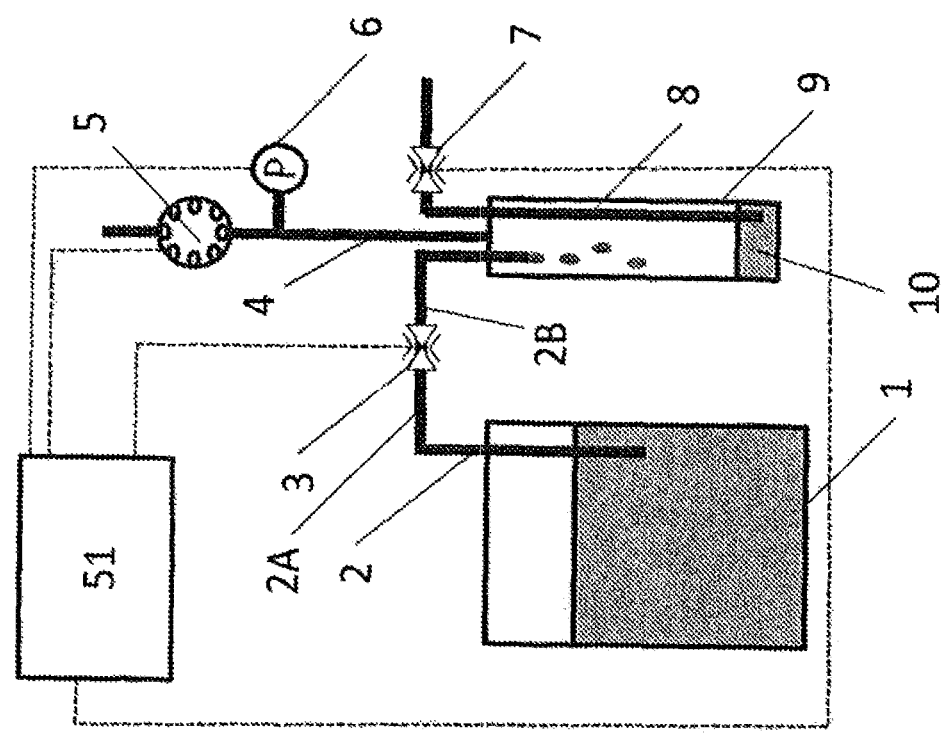
FIG. 2 is a schematic diagram of a third device for drawing a liquid from a process tank.

In FIG. 2, a third embodiment of a device for drawing a liquid from a process tank 1 is shown schematically. In addition to the process tank 1, the receptacle 9 and a first liquid line 2 connecting them with each other, which are also present in the embodiments described above, the device additionally comprises a valve assembly 3, which is arranged between the process tank 1 and the receptacle 9 in the direction of flow of the liquid, is designed to open or to block the liquid line 2 optionally and which separates the first liquid line into a first section 2A, starting from the process tank up to the valve assembly 3, and a second section 2B after the valve assembly 3 toward the first receptacle. A second liquid line 8, which opens into the first receptacle 9 and whose end that opens into the first receptacle 9 protrudes into the first receptacle 9 to the extent that it is immersed in a liquid 10 contained in the first receptacle 9. The end of the second liquid line 8, opening into the receptacle 9, can be designed, for example, as a riser. Also the liquid line 8 can be opened or closed by a valve assembly 7.

The first liquid line 2 opens into the receptacle 9 such that the liquid 9 that passes through the liquid line 2 into the receptacle traverses a gravity section as a rule. To this end, a first liquid line 2 opens into a region of the receptacle 9, which is clearly located above an expected level of the liquid 10 contained in the receptacle 9.

A gas line 4, which connects the receptacle with a gas pressure regulator 5 and a pressure sensor 6, opens into the receptacle 9. The pressure sensor 6 may be, for example, a gas pressure sensor. The pressure sensor 6 detects the gas pressure prevailing in the first receptacle 9 as the pressure sensor 6 communicates with the gas phase of the receptacle 9 via the gas line 4. Based on the measurement signal of the pressure sensor 6, the gas pressure prevailing in the receptacle 9 is monitored and/or adjusted or regulated to a predetermined value by means of the gas pressure regulator 5. In this case, the gas pressure is controlled such that it falls below the difference between the gas pressure prevailing in the process tank 1 and the effective hydrostatic differential pressure in accordance with equation (3) or (4) by at least a predetermined minimum value M (see equation (4)). This always ensures that the pressure difference $p_1-p_2$ between the pressure $p_1$ prevailing at the first end of the liquid line 1 and the pressure $p_2$ prevailing at the second end of the liquid line 2 is greater than zero or greater than or equal to a predetermined minimum value allowed.

The gas pressure regulator 5 may include a pump, in particular, a vacuum pump, a diaphragm pump, or a peristaltic pump. It may also comprise an electronic control or regulation circuit, which is configured to actuate the pump for setting a desired gas pressure, based on the measurement signal provided by the pressure sensor 6. A corresponding control circuit may also at least partially be a component of a higher-level control unit, e.g. process control or a transmitter, which is connected to the gas pressure regulator 5, and separated from, for example, the device for drawing the liquid from the process tank. As in the example shown here, it is also possible that such a remote control unit 51 is connected with the gas pressure regulator 5 and with the pressure sensor 6 for communication and receives and processes the measurement signal of the pressure sensor 6, as well as controls the gas pressure regulator 5.

In this example, the control unit 51 is also connected with the valve assemblies 3 and 6, and is used to operate the valve assembly 3, to release or to block the liquid transport from the process tank 1 to the first receptacle 9 or to open the valve assembly 6 for drawing liquid from the receptacle or block the removal of liquid from the first receptacle 9. The control unit 51 comprises a computer program, which can be executed by it and is used to control the device for drawing liquid from the process tank 1, in particular, the valve assemblies 3, 7 and the gas pressure regulator 5.

By means of the gas pressure regulator 5, a gas pressure, which falls below the difference between the gas pressure prevailing in the process tank 1 and the effective hydrostatic pressure difference, defined in equation (2), between the ends of the first liquid line by at least a predetermined minimum value, can be set in the receptacle 9. The predetermined minimum value corresponds to a minimum value which is required to transport liquid from the process tank 1 via the liquid line 2 into the receptacle 9. It depends, in particular, on the geometry of the liquid line, and on the level of the liquid in the process tank. The pressure prevailing at the first end of the liquid line can be equated in good approximation to the difference between the gas pressure prevailing in the process tank 1, which shows a known, slight overpressure or coincides with the ambient pressure in many cases of biochemical or biological processes which are carried out in bioreactors or fermenters as a process tank, in particular, for flexible tank walls in disposable fermenters, and said pressure difference $\Delta pHydro,1$ at the first end of the first liquid line, which can be determined in close approximation to the level of the liquid in the process tank and the geometry of the liquid line. A pressure measurement in the area of the first end of the liquid line 2 opening into the process tank 1 is, therefore, not necessary for the setting, control and/or regulation of the pressure difference, but of course, it is possible.

The pressure difference greater than zero between the first end of the liquid line 2, connected to the process tank 1, and the second end in the receptacle 9 is maintained during operation of the device shown in FIG. 2 and monitored by means of the measurement signal of the pressure sensor 6, as long as the first end of the liquid line 2 is connected to the process tank 1 and as long as the process tank 1 is to be protected from contamination, even if the valve assembly 3 closes the liquid line 2, so as to prevent transport of liquid through the second section 2B of the liquid line 2 after the valve assembly 3 toward the receptacle 9. As described above, this is used to ensure prevention of contamination of the process tank 1 even in case of failure of the valve assembly 3.

The fact that liquid within the first liquid line located in its first section 2A may flow back to the process tank cannot be completely ruled out in some cases even when the pressure difference between the first and the second ends of the first liquid line in the first operating mode and the second operating mode is greater than zero or is, in particular, a positive, permissible minimum value. This may be the case, for example, when the valve assembly 3 comprises a hose pinch valve, or in case of very large diameters of the first section 2a of the first liquid line. However, in cases of any return flow, only the non-contaminated liquid, drawn during a previous removal process, always flows back into the process tank, so as to effectively prevent any contamination of the process tank.

The control unit 51 can also be used to control the process carried out in the process tank 1. In this case, it can be designed to maintain the pressure difference between the process tank and the receptacle 9, and thus, also between the first and the second ends of the liquid line by means of the gas pressure regulator 5 greater than zero or above a predetermined minimum value in all phases of the process, where the process tank 1 is to be protected against any contamination. If the process carried out in the process tank 1 is controlled by means of a process control, for example, a remote process control computer, which is different from the control unit 51, such process control can be connected to the control unit 51 for communication. In this case, the control unit 51 may receive one or more control signals from the process control, based on which the control unit 51 can determine if the process tank 1 is to be protected against contamination at a given point of time or during a time interval, or not. Accordingly, the control unit 51 controls the device, among other things, by means of the gas pressure regulator 5 in such a way that the pressure difference between the first and the second ends of the liquid line 2 during the process phases, in which the process tank 1 is to be protected from contamination, or at any time is above zero or above a predetermined minimum value.

For drawing liquid from the process tank 1 in a first operating mode of the device, the pressure difference between the first and the second ends of the liquid line is increased by means of the liquid line 2, closed by the valve assembly 3. Thereafter, the liquid line 2 is released by means of the valve assembly 3, whereby liquid is transported from the process tank 1 through the liquid line 2 to the receptacle 9. The removal is terminated by closing the liquid line 2 again by means of the valve assembly 3. Increase in the signal of the pressure sensor 6 can be used to monitor the removal, in particular, to determine the removed volume of liquid. The removal can be done either by manual operation of the valve assembly 3 and the gas pressure regulator 5, or automatically by means of the already mentioned control unit 51. Removal of liquid may include drawing a predetermined volume of liquid. For example, the device can be operated such that predetermined volumes of liquid are repeatedly drawn from the process tank 1 at predetermined time intervals and transported into the receptacle 9. In each case, a longer sampling interval may exist between the withdrawals, during which the device is operated in a second operating mode, in which transport of liquid through the liquid line 2 is blocked by the valve assembly 3. Also in this second operating mode, the gas pressure in the first receptacle 9 can be set by means of the gas pressure regulator 5 such that a pressure difference, which does not fall below an allowed minimum value is present between the first and the second ends of the liquid line 2. All these process steps can be carried out automatically by means of the control unit 51.

Figure 3:
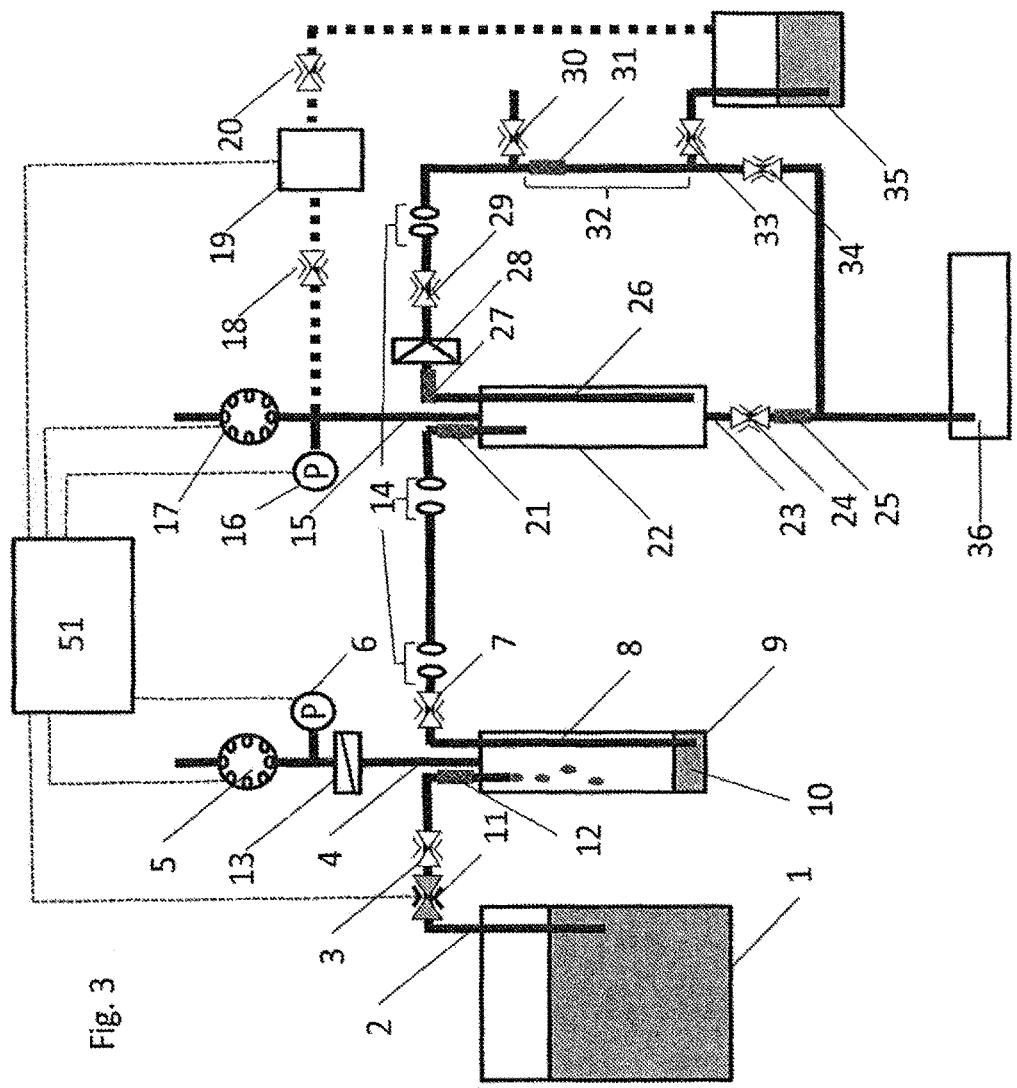
FIG. 3 is a schematic diagram of a system, comprising a device for drawing a liquid and a device for treatment of the drawn liquid.

In FIG. 3, a system that constitutes a device for drawing a liquid from a process tank and a device for treatment of the removed liquid is schematically illustrated. This system can be used, for example, as a sampling and sample preparation device for an analyzer, to which the extracted and treated liquid can be supplied as a liquid sample to perform analytical measurements.

The device for drawing a liquid from a process tank has a very similar design as that of the embodiment illustrated with reference to FIG. 2. Like reference numerals designate components with identical design. The device comprises a first liquid line 2, which connects a process tank 1 with a first receptacle 9 and whose first end opens into the process tank 1 and the second end opens into the first receptacle 9, as well as a valve assembly 3 that is used to either block or release the liquid transport through the liquid line 2. Moreover, the device comprises a sterile filter 13, which is arranged in the gas line 4 and separates the first receptacle 9 from the gas pressure regulator 5 and a pressure sensor 6, which may be designed identically to the embodiment shown with reference to FIG. 2. The sterile filter 13 can have a pore size of, for example, 0.2 microns.

In order to reduce the volume flow during removal of the liquid from the process tank 1, and thus, to increase the metering accuracy of the extracted liquid volume, the first liquid line 2 has a static and/or adjustable and/or controllable flow resistance 11, which can be implemented in the form of, for example, an adjustable electronically controlled hose pinch valve. With the first liquid line 2 open, namely during the refilling operation which can be carried out as already described with reference to FIG. 2, the flow resistance 11 can be controlled by determining the actual pressure increase in the first receptacle 9 by opening or closing the hose pinch valve.

A conductivity sensor 12, which can be used to control the filling of the first liquid line 2 with liquid 10 is arranged near the second end of the first liquid line 2 that opens into the first receptacle 9. Based on the signal of the conductivity sensor 12, it can be detected, in particular, whether liquid, gas or a liquid containing gas bubbles is present at the installation location of the conductivity sensor 12.

Likewise the embodiment illustrated with reference to FIG. 2, the device for extracting liquid from the process tank 1 comprises a control unit 51, which is connected to the controllable components, in particular, the valve assemblies 3, 7 and the flow resistance 11, as well as the sensors 11, 6, and the gas pressure regulator 5 for controlling them.

A second liquid line 8, which opens into the first receptacle 9 and whose end that opens into the first receptacle 9 is designed as a riser that protrudes into the first receptacle 9 to the extent that it is immersed in a liquid 10 contained in the first receptacle 9. Liquid 10, contained in the first receptacle 9 can be drawn via this second liquid line 8 and transferred to the treatment device. The line 8 can be opened or closed by a valve assembly 7.

In an advantageous embodiment, the first liquid line 2, the first receptacle 9, the gas line 4, the sterile filter 13 and the second liquid line 8 can be sterilized and replaced in the interconnected state. To this end, the liquid lines are mostly made of a hose made of a plastic material, such as PTFE, PFA or silicone. The liquid lines are made of a resilient plastic material such as silicone at least in the area of the valve assemblies 3, 7 for the liquid lines, which represent electromagnetic hose pinch valves in the advantageous embodiment.

The second liquid line 8 comprises at its end a coupling device 14, which is connected to another liquid line and by means of which the device for drawing a liquid from the process tank 1 can be connected with a device for treating a liquid. In the exemplary embodiment shown here, the coupling device 14 is connected to another liquid line, which is in turn connected with a third liquid line via a coupling device 14. The third liquid line opens into a second receptacle 22. This second receptacle 22 is part of the device for treating a liquid and is used to receive a liquid to be treated. Another conductivity sensor 21, which can be used to monitor the fill level of the third liquid line is arranged in the third liquid line. In this case, the measurement signal of the conductivity sensor 21 can be evaluated in the same way as that of the conductivity sensor 12.

The device for treating a liquid may be controlled by means of a higher-level control unit, which comprises, for example, a memory-programmable logic controller or a transmitter, so that the liquid treatment may be carried out automatically. This may be connected to the control unit 51 for communication. As shown in the example here, it is also possible that the control unit 51 takes control of the entire system, namely the device for withdrawing the liquid from the tank and the process tank for treatment of liquids. For this purpose, the control unit 51 has appropriate computer programs that can be executed by it.

A fourth liquid line 26, which opens into the second receptacle 22 and whose end that opens into the second receptacle 22 protrudes into the second receptacle 22 to the extent that it is immersed in a liquid contained in the receptacle 22. The fourth liquid line 26 is connected in a detachable way with a fifth liquid line 32 via a particle separation module 28 and a valve assembly 29 by means of another coupling device 14. The particle separation module 28 may comprise one or more membranes for the separation of particles from the liquid. In the fourth liquid line 26, another conductivity sensor 27 is located between the second receptacle 22 and the particle separation module 28.

The fifth liquid line 32 has a first branching point, which is designed, for example, as a T-piece, by means of which liquid can be removed from the fifth liquid line 32 and led, for example, to an analyzer. The branching liquid line can be shut off by a valve 30.

The fifth liquid line 32 has a second branching point, over which the liquid line 32 can be connected to a reservoir 35 containing a cleaning liquid. The fifth liquid line 32 can be shut off from the reservoir 35 by a valve assembly 33.

The second receptacle 22 is connected via a sixth liquid line 23 to a third receptacle 36 that is used to hold discarded liquid and/or used-up cleaning liquid. The sixth liquid line 23 can be closed by a valve assembly 24. Between the valve assembly 24 and the third receptacle 26, a conductivity sensor 25 is arranged, whose signal can be used to determine when the liquid contained in the second receptacle is completely emptied into the third receptacle 36.

The fifth liquid line 32 opens into the sixth liquid line 23 via a branching point that is arranged between the valve assembly 24 and the third receptacle, so that liquid that has not been drawn from the liquid line 32 via the first branching point can be discharged into the third receptacle. The fifth liquid line 32 can be shut off from the third receptacle 36 by the valve assembly 34.

A gas line, which connects a gas phase contained in the receptacle 22 with a gas pressure regulator 17 and a pressure sensor 26, opens into the second receptacle 22. The pressure sensor 26 is used to monitor the gas pressure prevailing in the receptacle 22. The gas pressure regulator 17 may include a pump, in particular, a diaphragm pump, peristaltic pump or vacuum pump. By means of the gas pressure regulator 17, a desired gas pressure can be set and/or regulated within the second receptacle 22.

In one embodiment (not shown here), the gas pressure regulator can be designed to selectively generate a positive or a negative pressure within the gas phase contained in the receptacle 22. Alternatively, as shown here, the gas line can be connected via a branch to another gas pressure regulator 19, which is designed to feed a pressurized gas, e.g. compressed air, to the second receptacle 22. For this purpose, the gas pressure regulator 19 can comprise a source of pressurized medium, for example, a source of compressed air. The gas line can be shut off from the other gas pressure regulator 19 by a valve assembly 18. The other gas pressure regulator 19 is connected with the reservoir 35, containing the cleaning liquid, via a gas line that can be closed by means of another valve assembly 20.

Likewise, the gas pressure regulator 5, the gas pressure regulator 17 and the gas pressure regulator 19 can comprise their own electronic control or regulation circuit, in particular, be designed to control the pump of the gas pressure regulator 17 or the source of pressurized medium of the gas pressure regulator 19 on the basis of the measurement signal of the pressure sensor 16, in such a manner that the desired gas pressure is set in the second receptacle 22. The higher-level control unit 51 may be connected to the control and regulation circuits of the gas pressure regulators 5, 17 and 19 for communication, so as to control them. Alternatively, the control or regulation circuit may be included wholly or partly in a higher-level control unit that is connected to the gas pressure regulator 17 and/or the gas pressure regulator 19.

Hereinafter, a method for the treatment of the liquid 10, which is drawn from the process tank 1 and transferred to the first receptacle 9, by means of the device described above will be explained in more detail. All process steps described can be carried out automatically by means of the control unit 51, which is connected with the valve assemblies 18, 29, 30, 33, 34, 23, the sensors 12, 21, 25, 27, 31 and the gas pressure regulators 17, 19 for controlling them using the sensor signals. For better clarity, the connections to the valve assemblies and the sensors are not shown in detail in FIG. 3.

The liquid 10, contained in the first receptacle 9 and drawn from the process tank 1, is transported via the second liquid line 8 into the second receptacle 22 by setting up a gas pressure that is less than the gas pressure in the first receptacle 9 using the gas pressure regulator 17 in the second receptacle 22, so that a set volume of the liquid 10 is transported to the second receptacle 22 once the valve assembly 7 is opened to release the second liquid line 8. The time of termination of the transportation process is determined from the measurement signal of the conductivity sensor 21, which is arranged in the third liquid line that opens into the second receptacle 22. The liquid transport is terminated when no more liquid is detected in the third liquid line using the measurement signal.

By setting an overpressure in the second receptacle 22 by means of the gas pressure regulator 19 and by opening the valve assemblies 18, 29 and 34, the liquid contained in the second receptacle is transported via the fourth liquid line 26, opening into the second receptacle 22, through the particle separation module 28 and the associated fifth liquid line 32 towards the third receptacle 36. Preferably, the liquid volume conveyed from the second receptacle 22 is dimensioned such that the fifth liquid line 32 is filled with liquid to such an extent that the volume needed in the subsequent analytical operation can be provided. The valve assemblies 30 and 33 are closed and block the drain for removal of liquid and the reservoir 35 from the fifth liquid line 32.

When passing through the particle separation module 28, the particles contained in the liquid cells, cell components and/or cell aggregates are separated by at least 25%, preferably 50%, more preferably 75%, based on the particle count in a predetermined volume of liquid. This is preferably accomplished by at least one membrane filtration by size exclusion, wherein the module comprises at least one sterile filter.

Based on the measurement signal of the conductivity sensor 27, which is arranged in the fourth liquid line 26 between the second receptacle 22 and the particle separation module 28, the transport of liquid is controlled by the particle separation module 28 such that no air enters the module at the end of the transportation process. Based on the measurement signal of the conductivity sensor 27, it can especially be determined whether the gas bubbles are contained in the pumped liquid. If the presence of gas bubbles or lack of liquid is found on the basis of the conductivity measurement, pumping of liquid from the second receptacle 22 is stopped immediately.

The valve assemblies 30 and 34 are opened to remove liquid from the fifth liquid line 32 through the first branch point of the fifth liquid line 32. The liquid can be drawn, for example, by means of a pump (not shown in the figure) that draws liquid from the fifth liquid line 32.

The bubble-free removal can be monitored by the conductivity sensor 31 that is arranged close to the branching point for removal. If the presence of gas bubbles or lack of liquid is found on the basis of the conductivity measurement, the subsequent analytical operation using the measurement system is not performed.

The system may be cleaned from time to time. For this purpose, overpressure is applied to the reservoir 35 by means of the gas pressure regulator 19 and/or a negative pressure is set at the second receptacle 22 by means of the gas pressure regulator 17. The opening of the valve assemblies 20, 33 and 29 leads to the transport of the cleaning liquid from the reservoir 35 in the direction of the second receptacle 22. In this case, the particle separation module 28 is backflushed with a cleaning liquid. This backwash can be designed such that a large pressure drop is realized on the one hand, causing flushing of the particle-filled pores of the one or more filter membranes of the particle separation module 28 (module 24 open) and/or filling the second receptacle 22 with a predetermined volume of cleaning solution (module 24 closed) and is then only emptied into the third receptacle 36 via the sixth liquid line 23. The emptying process is controlled by means of the signal of the conductivity sensor 25 which is arranged in the sixth liquid line 23.

As a cleaning liquid, pure water, preferably with a conductivity of 500 µs/cm to 700 µs/cm corresponding to that of tap water and/or phosphate buffered saline (e.g. 0.1 M phosphate buffer of pH 7.2 to pH 7.4 with 0.137 M NaCl and 2.7 mM KCl), and/or 10 mM tris-buffer and/or 0.5 mM sodium pyrophosphate with 0.7 mM tri-Na-EDTA can optionally be used in each case with at least 0.5 vol.-% of a surfactant such as Tween 20 or Tween 80. It may also be advantageous to use a highly concentrated, buffered saline (for example, 1 M to 3 M NaCl solution) as a cleaning liquid, which forces water from the interior of the cell-containing particles by the prevailing high osmotic pressure gradient and thus, causes a reduction in volume of the particles, so as to make it easier to remove them by backflushing. In another embodiment, the backflush operation can take place through the use of an additional temperature control for the cleaning liquid with a temperature gradient, by continuous heating of the cold cleaning liquid to at least 50° C. up to 80° C. during backflushing.

Depending on the application requirement, partial steps or entire sequences can be carried out, manually controlled by an operator (laboratory conditions), or repeatedly run automatically (industrial process conditions). For this purpose, the system shown in FIG. 3 may include one or more control units. For example, it is conceivable that the device for drawing liquid from the process tank 1 has a first electronic control unit, which at least partially controls the operation of the device. Likewise, the device for treating the liquid may comprise a second, additional electronic control unit, which at least partially controls the operation of this device. This control unit may be configured in the same way as the first control unit.

In addition or, as in this example, alternatively, the system illustrated in FIG. 3 may have a central control unit which controls at least the partial steps of operation of the system. This control unit can also be configured as a conventional computer, transmitter, programmable logic controller, or otherwise in the form of a suitable electronic data processing device.

Figure 4:
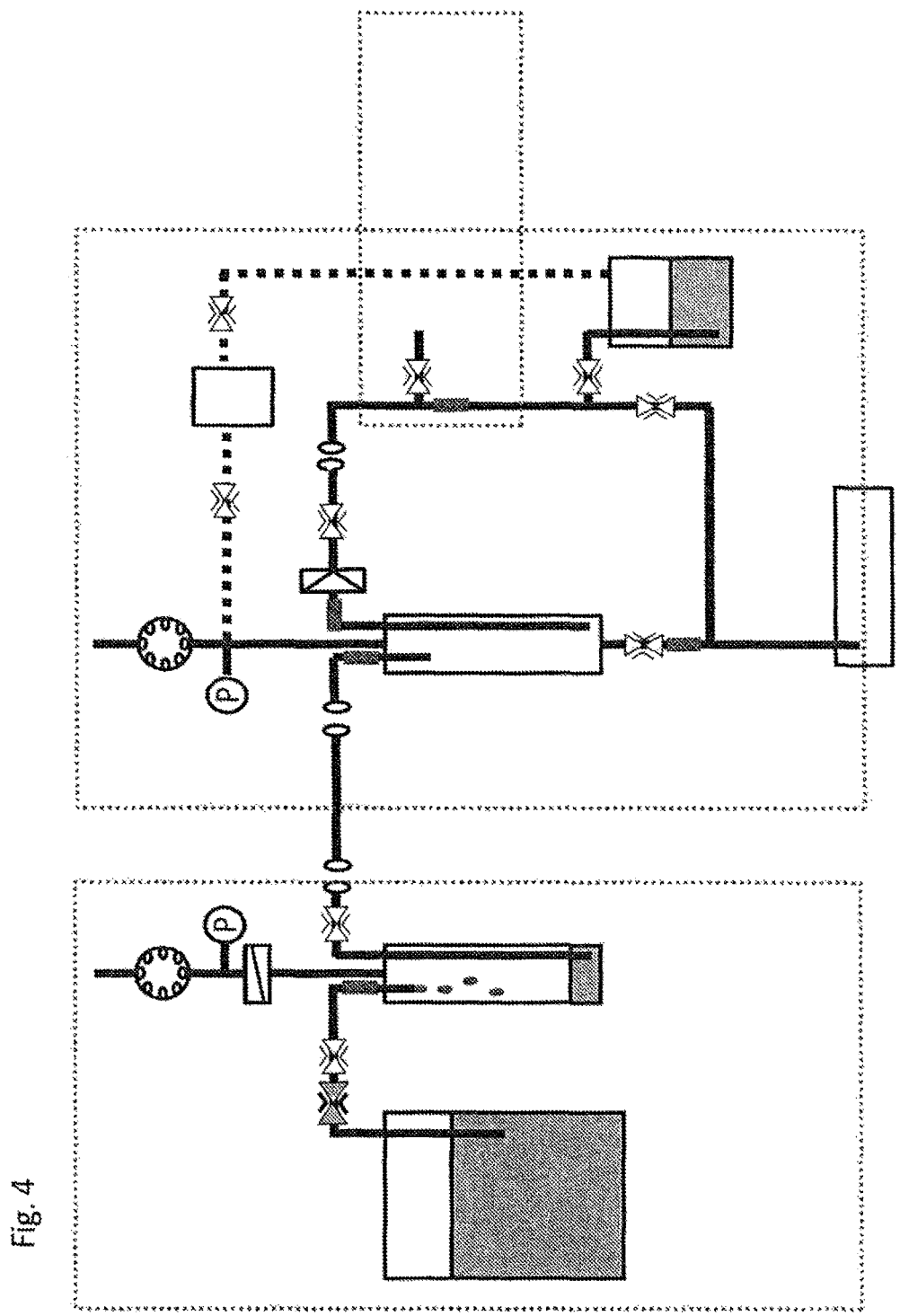
FIG. 4 is a schematic diagram of the system shown in FIG. 3 with illustration of a possible modular structure.

The device for drawing liquid from a process tank and/or the device for treating liquids may be constructed as modular units. In this way, they can be arranged interconnected, in particular, spatially separated from one another, via at least one liquid line. This is schematically indicated in FIG. 4 by the dashed rectangles circumscribing the modules. For better clarity, the control unit and the reference numerals are not shown in this figure. However, the details of the system shown in FIG. 4 coincide with those of the system shown in FIG. 3. This modular design allows combination of a single module with another device, adapted to the respective application. For example, the device for drawing fluids can be replaced with a sterilizable sampling valve, like the one described in DE 10 2006 19 242 A1, for applications in large-scale production processes.

Figure 5B:
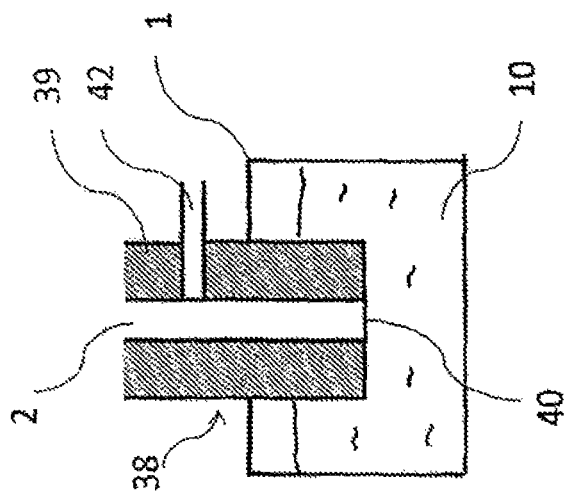
FIGS. 5a and 5b show a schematic drawing of a sluice valve in a first embodiment.

The first end of the first liquid line 2 can be connected with the process tank 1 by means of a sluice valve. Such a sluice valve can be used, for example, in all examples described previously with reference to FIGS. 1 to 4. A possible basic structure of such a sluice valve 38 is schematically shown in FIG. 5a and FIG. 5b.

Figure 5A:
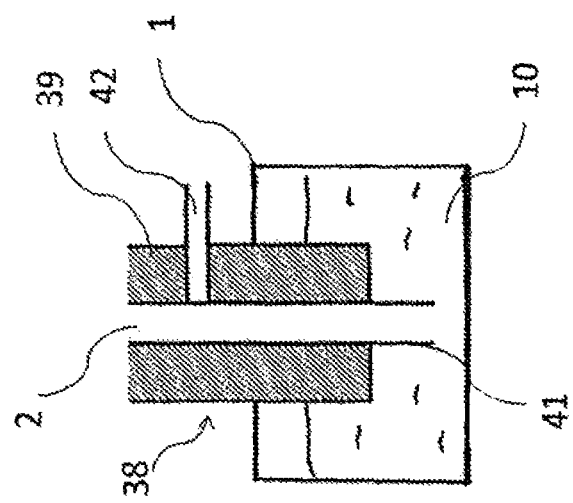

In FIG. 5a the sluice valve 38 is shown in a first position in which the first end of the first liquid line 2 is inserted into the process tank 1. The sluice valve 38 has a housing 39 that is attachable to the process tank 1. To this end, the process tank 1 can have, for example, a nozzle that is not shown here in detail. In the example shown here, the first end of the first liquid line 2 is designed as a front (process-side) end of a dip tube 41 that is axially movable in the housing 39 between the first position that is retracted into the process tank 1 as shown in FIG. 5a and the second position that is extended from the process tank 1 as shown in FIG. 5 b. To this end, the sluice valve 38 has a drive that is not shown here and can either be manually or automatically operated. At its process end, the dip tube 41 is open towards the process tank 1 and is immersed in the liquid 10 present in the process tank 1 such that in the first position of the dip tube (FIG. 5a), the liquid 10 is transported from the process tank 1 through the liquid line 2 in the direction pointed by the arrow, upon application of a pressure difference greater than or equal to an allowed minimum value between the first end of the first liquid line 2 and the second end of the first liquid line 2 that opens into the second receptacle 22.

In the second position of the dip tube 41 (FIG. 5b), the first end of the first liquid line 2 that is open on the process side is separated from the process tank 1 by means of a closure 40, so that no liquid 10 from the tank 1 can enter the first liquid line 2. This is realized by providing a locking mechanism, which closes the process-side opening of the housing 38, through which the dip tube 41 is guided for retraction into the process tank 1 during retraction of the dip tube 41.

The housing 39 may have another feed line 42, which opens into the liquid line 2. The feed line 42 can be used to equalize the pressure to allow transport of media, in particular, liquid through the first liquid line 2 also in the second position of the dip tube 41. Cleaning or sterilization media, e.g. hot steam can also be supplied to the first liquid line 2 via the feed line.

Figure 6A:
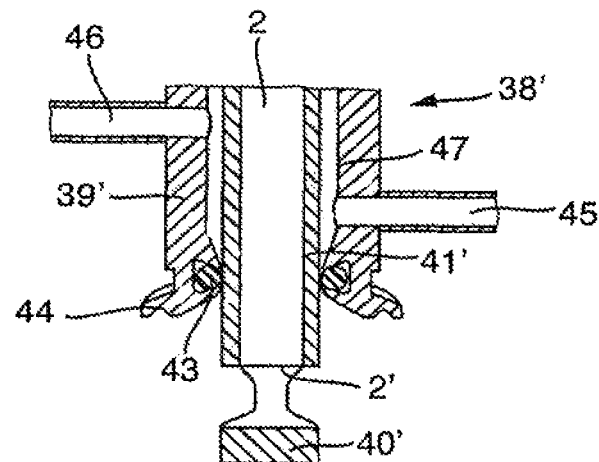
FIGS. 6a and 6b show a schematic drawing of a sluice valve in a second embodiment.
Figure 6B:
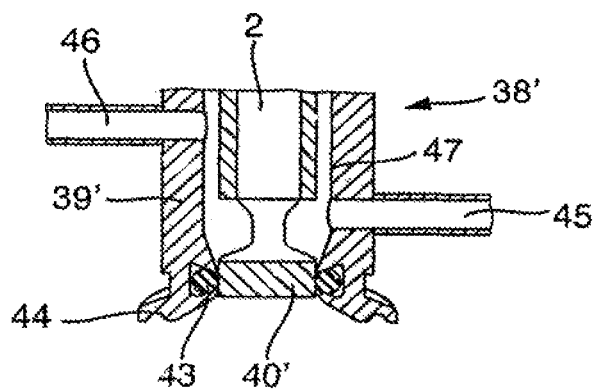

FIGS. 6a and 6b schematically illustrate another embodiment of a sluice valve 38' for use in a device for the removal of liquids from a process tank. The sluice valve 38' includes a housing 39', which can be connected with a complementary adapter of the process tank (not shown here) by means of a standardized connector 44. In the housing 39', a dip tube 41' is arranged axially movable between a first position that is retracted into the process tank (FIG. 6a) and a second position that is extended from the process tank (FIG. 6b). The dip tube 41' and the housing 39' can be made of, for example, stainless steel. In the dip tube 41', a terminal section 2' of the liquid line 2 that connects the process tank with the first receptacle is, for example, designed as a glass tube, and is arranged so as to be movable with the dip tube 41'. The process-side end of the glass tube forms the first end of the liquid line 2 at the same time.

At its process-side end, the dip tube 41' is connected via bars with a cylinder 40', which shuts off the process tank, in the second position of the dip tube 41' (FIG. 6b), from the interior of the housing and the end of the first liquid line 2 that is retracted into the housing interior by jointly acting with a seal 43 that is arranged within the housing 39'. In the first position of the dip tube 41' (FIG. 6a), the open end of the first liquid line 2 is in contact with the interior of the process tank. Here, the outer side of the dip tube 41' adjoins the seal 43 such that the interior of the housing 39' is shut off from the process tank also in this position. If the end of the first liquid line 2 is immersed in a liquid contained in the process tank, liquid can be transported from the process tank to the first receptacle, upon application of a pressure difference between the first end of the first liquid line 2 and the second end of the first liquid line 2 that opens into the first receptacle.

Inside the housing is a chamber 47, to which a feed line 45 and a discharge line 46 lead. Cleaning or disinfecting media can be introduced through the feed line 45 into the chamber 47 to clean and/or disinfect the chamber and/or the first liquid line 2. The supply and discharge pipes may also be used as pressure equalization pipes to allow liquid transport through the first liquid line 2 also in the second position of the sluice valve 38'.

The device, described with reference to FIGS. 2 to 4, for drawing liquid from a process tank may comprise such a sluice valve, by means of which the first end of the first liquid line 2 can be connected to the process tank. This sluice valve can be provided in addition to the valve assembly 3.

For withdrawing the liquid during normal operation of the device, the process-side end of the dip tube 41, forming the first end of the first liquid line, is preferably, always retracted in the process tank 1; thus the dip tube is in its first position (FIG. 5*a*). In this position, the first end of the first liquid line 2 is connected to the process tank 1. In the second position of the dip tube 41, it is possible to separate the first end of the first liquid line 2 from the process tank 1 for a prolonged duration to perform cleaning or sterilization. In this position, the pressure difference between the first and the second ends of the first liquid line 2 can be adjusted such that it is greater than or equal to an allowed minimum value. However, it is also possible to let the pressure difference fall below a minimum value in this position of the dip tube.

In the example described here, the sluice valve is also operated by means of the control unit 51. Therefore, the control unit 51 has information about when the first end of the liquid line 2 is connected to the process tank, and therefore, also when to maintain a pressure difference greater than zero between the first and second ends of the first liquid line 2, at least as long as the process tank 1 must be protected from contamination, and in which phases the first end of the liquid line 2 is not connected to the process tank 1 so that the differential pressure can also fall below the minimum value.

What is claimed is:

1. A liquid sample drawing device, comprising:
   a receptacle embodied to receive and to contain a liquid sample;
   a liquid line having a first end and a second end, wherein the first end is embodied to connect to a process tank, and wherein the second end opens into the receptacle;
   a valve assembly disposed in the liquid line between the first end and the second end, wherein the valve assembly is configured to selectively block or allow liquid transport through the liquid line;
   a pressure sensor connected with the receptacle and configured to measure a pressure within the receptacle and to output a pressure measurement signal based on the measured pressure;
   a gas pressure controller connected with the receptacle via a gas line opening into the receptacle, wherein the gas pressure controller is configured to control and to regulate a gas pressure in the receptacle; and
   a control unit configured to receive the pressure measurement signal from the pressure sensor and further configured to control the valve assembly and the gas pressure controller,
   wherein the control unit is further configured to regulate and to control, based on the pressure measurement signal, a pressure difference $pI-p2$ between a pressure $pi$ at the first end of the liquid line and a pressure $p2$ at the second end of the liquid line to be greater than a predetermined minimum value, said predetermined minimum value being greater than zero,
   wherein the control unit is further configured to operate in a first operating mode of configuring the valve assembly to allow liquid transport through the liquid line and of configuring the gas pressure controller to control the pressure difference $p1-p2$ to be greater than the predetermined minimum value, and
   wherein the control unit is further configured to operate in a second operating mode of configuring the valve assembly to block liquid transport through the liquid line and of configuring the gas pressure controller to control the pressure difference $p1-p2$ to be greater than the predetermined minimum value.

2. The liquid sample drawing device of claim 1, wherein the control unit includes a control signal input, and wherein the control unit is further configured to control the pressure difference $p1-p2$ when a control signal connected to the control signal input is asserted.

3. The liquid sample drawing device of claim 1, further comprising:
   a sluice valve disposed at the first end of the liquid line, wherein the sluice value is embodied to connect the first end of the liquid line to the process tank.

4. The liquid sample drawing device of claim 1, wherein the pressure sensor is a gas pressure sensor configured to measure a gas pressure within the receptacle, and wherein the pressure measurement signal is derived from the gas pressure within the receptacle.

5. The liquid sample drawing device of claim 1, further comprising:
   a sterile filter disposed within the gas line between the gas pressure controller and the receptacle.

6. The liquid sample drawing device of claim 1, further comprising:
   a controllable flow resistance disposed in the liquid line between the first end and the second end.

7. The liquid sample drawing device of claim 6, wherein the controllable flow resistance includes a pinch valve.

8. The liquid sample drawing device of claim 1, wherein the liquid line opens into the receptacle at a top of the receptacle.

9. A system for drawing a liquid from a process tank such that the process tank is protected from contamination, comprising:
   a liquid sample drawing device, comprising:
   a first receptacle embodied to receive and to contain a liquid sample; a first liquid line having a first end and a second end, wherein the first end is embodied to connect to a process tank, and wherein the second end opens into the first receptacle;
   a second liquid line having a first end and a second end, wherein the first end of the second liquid line opens into the first receptacle, a valve assembly disposed in the first liquid line between the first end and the second end, wherein the valve assembly is configured to selectively block or allow liquid transport through the first liquid line;
   a pressure sensor connected with the first receptacle and configured to measure a pressure within the first receptacle and to output a pressure measurement signal based on the measured pressure;
   a gas pressure controller connected with the first receptacle via a gas line opening into the first receptacle, wherein the gas pressure controller is configured to control and to regulate a gas pressure in the first receptacle; and
   a control unit configured to receive the pressure measurement signal from the pressure sensor and further configured to control the valve assembly and the gas pressure controller,
   wherein the control unit is further configured to regulate and to control, based on the pressure measurement signal, a pressure difference $pi-p2$ between a pressure $pi$ at the first end of the first liquid line and a pressure $p2$ at the second end of the first liquid line to be greater than a predetermined minimum value, said predetermined minimum value being greater than zero,
   wherein the control unit is further configured to operate in a first operating mode of configuring the valve assembly to allow liquid transport through the first liquid line and of configuring the gas pressure controller to control the pressure difference pI–p2 to be greater than the predetermined minimum value, and wherein the control unit is further configured to operate in a second operating mode of configuring the valve assembly to block liquid transport through the first liquid line and of configuring the gas pressure controller to control the pressure difference pI–p2 to be greater than the predetermined minimum value; and a liquid treatment device configured to treat a liquid drawn from the process tank, wherein the second end of the second liquid line is connected via a coupling device to the liquid treatment device.

10. The system according to claim 9, wherein the liquid treatment device includes a particle separation module designed to separate particles from the liquid drawn from the process tank.

11. The system according to claim 9, wherein the liquid treatment device includes a second receptacle and a gas pressure control mechanism connected with the second receptacle, wherein the gas pressure control mechanism is configured to set a gas pressure in the second receptacle, and wherein the liquid treatment device further includes a third liquid line opening into the second receptacle and connected with the second liquid line.

12. The system according to claim 10, wherein the particle separation module includes a sterile filter configured to separate particles from the liquid drawn from the process tank.

13. The system according to claim 11, wherein the liquid treatment device includes a fourth liquid line opening into the second receptacle and connected with a fifth liquid line via the particle separation module, and wherein the fifth liquid line includes a branching point over which liquid can be drawn from the fifth liquid line.

14. The system according to claim 9, wherein the first liquid line and the second liquid line each include a conductivity sensor configured to detect a fill level of the respective liquid line.

15. The system according to claim 9, wherein the liquid sample drawing device and the liquid treatment device are designed as a module separable from the rest of the system, and wherein the module is arranged spatially separated from the rest of the system and connected with the rest of the system via liquid lines.

16. A method for operating a liquid sample drawing device, comprising:
providing a liquid sample drawing device, comprising:
a receptacle embodied to receive and to contain a liquid sample; a liquid line having a first end and a second end, wherein the first end is embodied to connect to a process tank, and wherein the second end opens into the receptacle;
a valve assembly disposed in the liquid line between the first end and the second end, wherein the valve assembly is configured to selectively block or allow liquid transport through the liquid line;
a pressure sensor connected with the receptacle and configured to measure a pressure within the receptacle and to output a pressure measurement signal based on the measured pressure;
a gas pressure controller connected with the receptacle via a gas line opening into the receptacle, wherein the gas pressure controller is configured to control and to regulate a gas pressure in the receptacle; and
a control unit configured to receive the pressure measurement signal from the pressure sensor and further configured to control the valve assembly and the gas pressure controller,
wherein the control unit is further configured to regulate and to control, based on the pressure measurement signal, a pressure difference pi–p2 between a pressure pi at the first end of the liquid line and a pressure p2 at the second end of the liquid line to be greater than a predetermined minimum value, said predetermined minimum value being greater than zero,
wherein the control unit is further configured to operate in a first operating mode of configuring the valve assembly to allow liquid transport through the liquid line and of configuring the gas pressure controller to control the pressure difference pI–p2 to be greater than the predetermined minimum value, and
wherein the control unit is further configured to operate in a second operating mode of configuring the valve assembly to block liquid transport through the liquid line and of configuring the gas pressure controller to control the pressure difference pI–p2 to be greater than the predetermined minimum value;
connecting a process tank with the receptacle, wherein the connecting includes connecting the first end of the liquid line with the process tank;
measuring a pressure within the receptacle using the pressure sensor; transporting the liquid from the process tank to the receptacle in the first operating mode of the liquid sample drawing device;
blocking the transport of liquid from the process tank to the first receptacle in the second operating mode of the liquid sample drawing device; and
controlling the pressure difference pI–p2 to be greater than the predetermined minimum value in both the first operating mode and in the second operating mode when the first end of the liquid line is connected to the process tank and when the process tank is to be protected from contamination.

17. The method according to claim 16, further comprising:
controlling the pressure difference p1–p2 using the pressure measurement signal such that the pressure difference p1–p2 is greater than the predetermined minimum value.

18. The method according to claim 16, wherein controlling the pressure difference p1–p2 in the first operating mode and in the second operating mode includes generating or controlling a gas pressure in the receptacle such that the pressure p2 at the second end of the liquid line is lower than the pressure p1 at the first end of the liquid line by at least the predetermined minimum value.

19. The method according to claim 16, further comprising:
transporting a defined volume of the liquid from the process tank to the receptacle, wherein the transporting includes:
blocking the liquid line;
increasing the pressure difference p1–p2 between the first end and the second end of the liquid line;
unblocking the liquid line whereby the liquid is transported from the process tank towards the receptacle; and blocking the liquid line to maintain the pressure difference p1–p2 above the predetermined minimum value.

20. The method according to claim 19, further comprising:
determining a volume of the liquid transported from the process tank based on an increase in gas pressure in the receptacle detected by the pressure sensor during the liquid transport.

* * * * *